United States Patent [19]

Crossley

[11] 4,134,984

[45] Jan. 16, 1979

[54] THIAZOLE COMPOSITIONS

[75] Inventor: Roger Crossley, Reading, England

[73] Assignee: John Wyeth & Brother Limited, Maidenhead, England

[21] Appl. No.: 740,634

[22] Filed: Nov. 10, 1976

[30] Foreign Application Priority Data

Nov. 18, 1975 [GB] United Kingdom .............. 47481/75
May 28, 1976 [GB] United Kingdom .............. 22479/76

[51] Int. Cl.² .................... A61K 31/425; C07D 277/38
[52] U.S. Cl. ............................ 424/270; 260/306.8 R
[58] Field of Search .......................................... 424/270

[56] References Cited

U.S. PATENT DOCUMENTS 3,244,723   4/1966   Johnson et al. ................... 260/306.8

Primary Examiner—Frederick E. Waddell

[57] ABSTRACT

The invention relates to the use of thiazoles in the treatment of ulcers and/or hypersecretion in mammals. The invention also provides in a preferred aspect a pharmaceutical composition for use in the treatment of ulcers or hypersecretion comprising a compound of formula I

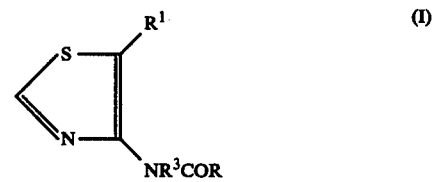

where $R^1$ is hydrogen, alkyl of 1-6 carbon atoms, or phenyl, R is hydrogen, n-alkyl of 1-4 carbon atoms (which may be substituted by chlorine), or cyclopropyl, $R^3$ is hydrogen or $COR^4$ where $R^4$ is as defined for R and R and $R^4$ may be the same or different and a pharmaceutically acceptable carrier.

17 Claims, No Drawings

THIAZOLE COMPOSITIONS

The invention relates to novel pharmaceutical compositions with anti-ulcer or anti-secretory activity and methods of treating ulcers and/or hypersecretion in an afflicted mammal.

Johnson and Nasutavicus (J. Org. Chem. 1963, 28, 1877–83), have described a new synthesis of 2-bromo-4-aminothiazoles. In U.S. Pat. No. 3,244,723 the same authors have described thiazoles, including 4-aminothiazoles and 2-bromo-4-aminothiazoles, with various biological activities namely against fungus, brown root, bean aphid, two spotted spider mite, plum curculio, northern fat-headed monnow and waterplantcoontail. No pharmaceutical applications of any of these compounds have been reported so far as I am aware. I have now surprisingly found that some 4-acylamino thiazoles falling within the class of compounds disclosed in U.S. Pat. No. 3,244,723 have anti-ulcer or anti-secretory activity whereas other closely related compounds are inactive. I have also found that certain novel 4-acylaminothiazoles possess anti-secretory activity.

Anti-ulcer activity was determined by the stress-induced erosion test of Senay & Levine, Proc.Soc.Exp.Biol.Med., 124, 1221-3 (1967) and anti-secretory activity by the test of H. Shay, D. Sun and H. Greenstein, Gastroenterology, 1954, 26, 903-13. The compounds which possess one or both these activities are considered to be anti-ulcer agents.

The present invention provides a pharmaceutical composition comprising a compound of formula I

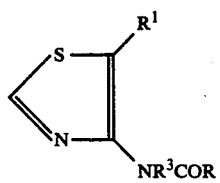

(I)

wherein $R^1$ is hydrogen, alkyl of 1–6 carbon atoms, or phenyl and R is hydrogen, n-alkyl of 1–4 carbon atoms (which may be substituted by chlorine, bromine, trifluoromethyl, methoxy, ethoxy, hydroxy, or cyano), alkenyl of 2–4 carbon atoms, alkynyl of 2–4 carbon atoms or cyclopropyl, $R^3$ is hydrogen or $COR^4$ where $R^4$ is as defined for R, and R and $R^4$ may be the same or different, and a pharmaceutically acceptable carrier.

In the compounds of formula I, $R^1$ may be methyl, ethyl, n-propyl, iso-propyl, n, s- or t-butyl, pentyl or hexyl.

In the compounds of formula I examples of R are for the alkyl group methyl, ethyl, n-propyl and n-butyl with methyl being preferred; for the alkenyl group vinyl, prop-1-enyl, but-1-enyl and but-2-enyl; for the alkynyl group ethynyl, prop-2-ynyl and but-2-ynyl.

When the term "lower alkyl" is used in this specification either alone or as part of another radical it means an alkyl group of 1 to 6 carbon atoms which may have a straight or branched chain e.g. methyl, ethyl, n-propyl, iso-propyl, n-butyl, s-butyl, t-butyl, n-pentyl, or n-hexyl.

Preferably the pharmaceutical composition is in unit dosage form e.g. as tablets or capsules.

The pharmaceutical compositions are distinguished from known insecticidal or anti-fungal compositions since these are not formulated to pharmaceutical standards nor are they in unit dosage forms.

For the pharmaceutical carrier any suitable carrier known in the art can be used to prepare the pharmaceutical compositions. In such a composition, the carrier may be a solid, liquid or mixture of a solid and a liquid. Solid form compositions include powders, tablets and capsules. A solid carrier can be one or more substances which may also act as flavouring agents, lubricants, solubilisers, suspending agents, binders, or tablet disintegrating agents; it can also be an encapsulating material. In powders the carrier is a finely divided solid which is in admixture with the finely divided active ingredient. In tablets the active ingredient is mixed with a carrier having the necessary binding properties in suitable proportions and compacted in the shape and size desired. The powders and tablets preferably contain from 5 to 99, preferably 10–80% of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax, and cocoa butter. The term "composition" is intended to include the formulation of an active ingredient with encapsulating material as carrier to give a capsule in which the active ingredient (with or without other carriers) is surrounded by carrier, which is thus in association with it. Similarly cachets are included.

Sterile liquid form compositions include sterile solutions, suspensions, emulsions, syrups and elixirs. The active ingredient can be dissolved or suspended in a pharmaceutically acceptable carrier, such as sterile water, sterile organic solvent or a mixture of both. The active ingredient can often be dissolved in a suitable organic solvent, for instance aqueous propylene glycol containing from 10 to 75% of the glycol by weight is generally suitable. In other instances compositions can be made by dispersing the finely-divided active ingredient in aqueous starch or sodium carboxymethyl cellulose solution, or in a suitable oil, for instance arachis oil.

Preferably the pharmaceutical composition is in unit dosage form, the composition is sub-divided in unit doses containing appropriate quantities of the active ingredient; the unit dosage form can be a packaged composition, the package containing specific quantities of compositions, for examples packeted powders or vials or ampoules. The unit dosage form can be a capsule, cachet or tablet itself, or it can be the appropriate number of any of these in packaged form. The quantity of active ingredient in a unit dose of composition may be varied or adjusted from 25 mg. to 500 mg. or more, according to the particular need and the activity of the active ingredient. Preferably the amount of active ingredient in a unit dose varies from 50 to 250 mg. The invention also includes the compounds in the absence of carrier where the compounds are in unit dosage form.

The anti-ulcer compositions of the invention will be administered orally in either liquid or solid composition form. These compositions may include one or more antacid ingredients e.g. aluminium hydroxide, magnesium hydroxide or bismuth carbonate, aluminium glycinate, calcium carbonate, magnesium trisilicate, sodium bicarbonate or the alumina gel described in British Specification No. 1,284,394.

The preferred compounds of formula I used in the pharmaceutical compositions of the invention are those in which R is hydrogen or methyl, and $R^3$ is hydrogen or COR where R is hydrogen or methyl. Preferably $R^1$ is hydrogen or methyl.

Preferred compounds used in the pharmaceutical compositions of the invention are 4-acetamidothiazole, 4-acetamido-5-methylthiazole, 4-propionamidothiazole, 4-formamidothiazole and 4-diacetamidothiazole.

The compounds of formula I where $R^3$ is hydrogen may be prepared by known methods e.g. by acylation of the corresponding 4-aminothiazoles of formula II

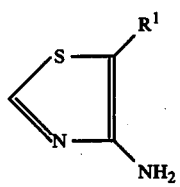

where $R^1$ is as previously defined.

Standard acylating agents capable of introducing the group RCO may be used e.g. the acid chloride RCOCl or acid anhydride

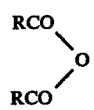

or mixed anhydride

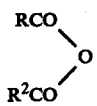

where R is as defined above and $R^2$ is another R group. When the group R is alkyl carrying a substituent functional group then one such group may be converted to another by standard methods.

A compound of formula I, where $R^3$ is $COR^4$ may be prepared by acylation of a compound of formula I where $R^3$ is hydrogen. The acylation may be carried out as discussed above. The products may be represented by formula V

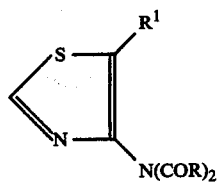

where $R^1$ and R are as defined in connection with formula I and each R radical may be the same or different.

Preferably R is hydrogen or unsubstituted n-alkyl of 1-4 carbon atoms e.g. methyl Some compounds of formula I are known compounds which are described in the literature reference mentioned above, in U.S. Pat. No. 3,244,723 or by Erlenmeyer et al Helv.Chim. Acta, 29, 1229-31.

Alternatively the compounds of formula I may be prepared by debromination of the corresponding 2-bromo compounds of formula III

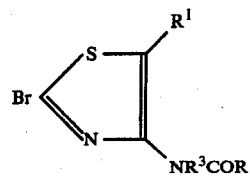

where $R^1$, $R^3$ and R are as defined in connection with formula I. The debromination may be carried out by treating the 2-bromo-4-acylaminothiazole or 2-bromo-4-diacylaminothiazole in an inert solvent with a suitable reducing agent e.g. sodium amalgam or hydrogen in the presence of a hydrogenation catalyst such as platinum, palladium or nickel and a base e.g. an organic base such as pyridine, or triethylamine, an alkali-metal carbonate or sodium acetate, to remove the hydrobromic acid. Suitable solvents include the lower alkanols such as methanol or ethanol, acetic acid, or aqueous dioxan.

The starting compounds of formula III where R is methyl or ethyl are described in J. Org. Chem. 1963, 28, 1877-83 or may be prepared by analogous methods. These compounds are also described in U.S. Pat. No. 3,244,723 which also describes the debromination reaction mentioned above.

The invention includes novel compounds of formula I wherein R is hydrogen and also the corresponding 2-bromo compounds which are intermediates for their preparation. Thus the novel compounds can be represented by formula VI

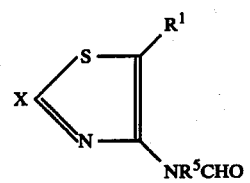

wherein $R^1$ is hydrogen, lower alkyl or phenyl, X is hydrogen or bromine and $R^5$ is hydrogen or COR where R is as defined in connection with formula I.

$R^1$ may have any of the values discussed in connection with formula I. Preferred compounds are those of formula IV

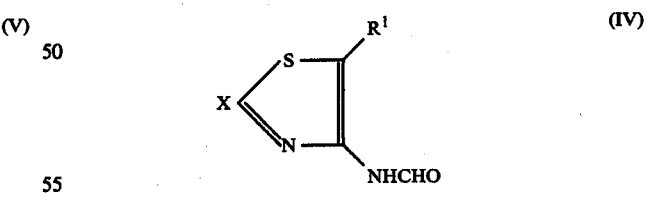

where $R^1$ and X are as defined in connection with formula VI, especially 4-formamidothiazole and 2-bromo-4-formamidothiazole.

The invention includes methods of preparing compounds of formula VI. For instance, a method of preparing a compound of formula VI wherein X is hydrogen by debromination of the corresponding compound wherein X is bromine as described above for compounds of formula I. Also included in the invention is a method of preparing a compound of formula IV wherein X is bromine by formylation of a corresponding 4-amino compound of formula VII

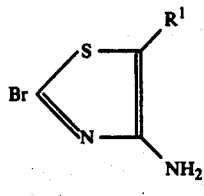

where R¹ is as defined above. This may be achieved by use of the mixed anhydride of formic acid and acetic acid which can be produced from formic acid in acetic anhydride. The invention further includes a method of preparing a compound of formula VI where R⁵ is COR which comprises acylating a compound of formula IV.

Compounds of formula VI where R⁵ is COR and X is bromine may also be prepared by formylation of a compound of formula VIII

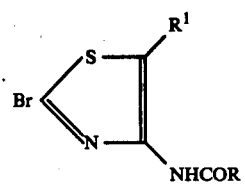

where R¹ and R are as defined in connection with formula VI.

Further novel compounds of formula I are those in which R is an n-alkyl group of 1-4 carbon atoms which is substituted as defined in connection with formula I except chloro and bromo alkyl. Also those in which R is alkenyl of 2-4 carbon atoms or alkynyl of 2-4 carbon atoms or cyclopropyl, are included. These compounds may be prepared as described above.

Pharmacological Test Results

When tested orally in rats 4-acetamidothiazole showed good activity at 100 mpk in the test of Brodie & Hanson mentioned above. The compound displayed outstandingly good anti-secretory activity in the test of Shay et al at 30 mpk. 4-Acetamido-5-methylthiazole was inactive at 100 mpk in the test of Senay & Levine but displayed activity in the anti-secretory test of Shay et al at 10 mpk. 4-Formamidothiazole was inactive in the test of Senay & Levine at 100 mpk but displayed good activity in the test of Shay et al down to 3 mpk.

Table 1

| Compound | Stress-induced erosion test (Senay & Levine) | | Anti-secretory (Shay et al) | | | | |
|---|---|---|---|---|---|---|---|
| | mpk p.o. | % Inhib | mpk ID | Vol | Conc | Free H⁺ | Total H⁺ |
| 4-acetamidothiazole | 100 | 67 | 30 | −85% | Insuff. for titration | | |
| | 30 | 30 | 10 | | Inactive | | |
| 4-acetamido-5-methyl-thiazole | 100 | Inactive | 30 | −52% | −32% | −61% | −52% |
| | | | 10 | −48% | −19% | −57% | −52% |
| | | | 3 | Inactive | | | |
| 4-formamidothiazole | 100 | Inactive | 30 | −92% | Insuff. | for | titration |
| | | | 10 | −44% | −28% | −59% | −46% |
| | | | 3 | −37% | −6NS | −3ONS | −35% |
| 4-acetamido-5-phenyl-thiazole | 100 | Inactive | 30 | −41% | −10%NS | −31% | −36% |
| 4-propionamido-thiazole | 100 | Inactive | 30 | −63% | −31%NS | −69% | −60% |
| | | | 10 | Inactive | | | |
| 4-cyclopropylcarbox-amidothiazole | 100 | 60 | 30 | −42% | −18% | −52% | −37% |

NS = Not significant

The following closely related compounds were inactive in the above tests [Senay & Levine (100 mpk) Shay (30 mpk)], 2-bromo-4-formamidothiazole, 4-amino-2-bromo 5-methylthiazole hydrobromide, 4-benzamido-2-bromothiazole, 4-acetamido-2-bromo-5-phenylthiazole, 4-isobutyr-amidothiazole, 4-benzamidothiazole.

When tested orally in rats 4-diacetamidothiazole showed moderate activity at 100 mpk in the test of Brodie & Hanson mentioned above. The compound displayed very good anti-secretory activity in the test of Shay et al at 30 mpk.

Table 2

| Compound | Stress-induced erosion test (Senay & Levine) | | Anti-secretory (Shay et al) | | | | |
|---|---|---|---|---|---|---|---|
| | mpk p.o. | % Inhib | mpk ID | Vol | Conc | Free H⁺ | Total H⁺ |
| 4-diacetamido-thiazole | 100 | 63 | 30 | −70% | Insuff. | for | titration |
| | 30 | Inactive | 10 | | Inactive | | |
| 4-butyramido-thiazole | 100 | 43 NS | 30 | −33% | −14% | −42% | −36% |
| 4-chloroacetamido-thiazole | 100 | 57 | 30 | | Inactive | | |

NS = Not significant

The invention also includes a method of treating ulcers and/or hypersecretion in an afflicted mammal which method comprises administering to said mammal an effective amount of a compound of formula I as defined above.

The amount of compound used will depend on the activity of the compound and the needs of the mammal being treated. Doses may range from 3 to 100 mg/kg.

Preferably the compound used is 4-acetamido-thiazole, 4-formamidothiazole, 4-acetamido-5-methylthiazole or 4-diacetamidothiazole.

The following examples illustrate pharmaceutical compositions in accordance with the invention.

EXAMPLE A

| Suspension | % w/v |
|---|---|
| Aluminium hydroxide gel B.P. 5% $Al_2O_3$ | 80% = 4% $Al_2O_3$ |
| Magnesia Magma 12% w/v MgO | 10% |
| 4-acetamidothiazole | 2.0% |
| Glycerin B.P. | 3.0% |
| Alcohol 60 O.P.* | 0.08% |
| Peppermint oil B.P. | 0.015% |
| Saccharin sodium B.P. | 0.01% |
| Methyl p-hydroxybenzoate sodium salt | 0.1% |
| Propyl p-hydroxybenzoate sodium salt | 0.02% |
| Butyl p-hydroxybenzoate sodium salt | 0.01% |
| Water q.s. ad | 100.00% |

*O.P. denotes overproof. 60 O.P. represents 91% w/v Ethanol/Water.

The above suspension is prepared by the following procedure. Add to the Alumina gel Magnesia Magma followed by the thiazole dispersed in glycerin, the peppermint oil dissolved in alcohol, the saccharine sodium dissolved in water, and the p-hydroxybenzoates dissolved in water. Make up to volume of water and stir well. Dose: 5 ml. t.d.s.

EXAMPLE B

| Antacid Tablet (chewable) | |
|---|---|
| Saccharin | 1.0 mg. |
| Hydrated alumina sucrose powder | 750.0 mg. |
| 4-acetamido-thiazole | 100.0 mg. |
| Mannitol B.P. | 170.0 mg. |
| Maize starch B.P. dried | 30.0 mg. |
| Talc. purified B.P. | 28.0 mg. |
| Magnesium stearate B.P. | 20.0 mg. |
| Peppermint oil B.P. | 1.0 mg. |
| | 1100.0 mg. |

Antacid tablets of the above formulation are prepared by the following procedure.

Triturate peppermint oil with talc (screen 40 mesh). Add the triturate, and other ingredients to a blender and mix thoroughly.

Slug the powder to large hard slugs.

Granulate the slugs through a 14 mesh screen.

Compress the granules on a suitable compression machine to give tablets of the required size.

EXAMPLE C

| Anti-ulcer tablet (without antacid) | mg/tablet |
|---|---|
| 4-acetamidothiazole | 100 mg. |
| Cellutab | 147.5 mg. |
| Mag. Stearate | 2.5 mg. |
| | 250.0 mg. |

The tablets are prepared by the following method.

Blend the ingredients in a suitable blender. Compress the blended ingredients on a suitable compression machine to form tablets of the above composition.

Celutab is a commercial product comprising 90–2% dextrose. 3–5% maltose remainder higher glucose saccharides. Spray crystallised.

EXAMPLE D

A suspension is prepared as described in Example A but replacing 4-acetamidothiazole by 4-acetamido-5-methylthiazole.

EXAMPLE E

An antacid tablet is prepared as described in Example B but replacing 4-acetamidothiazole by 4-acetamido-5-methylthiazole.

EXAMPLE F

An anti-ulcer tablet is prepared as described in Example C but replacing 4-acetamidothiazole by 4-acetamido-5-methylthiazole.

EXAMPLE G

A suspension is prepared as described in Example A but replacing 4-acetamidothiazole by 4-formamidothiazole.

EXAMPLE H

Antacid tablets are prepared as described in Example B but replacing 4-acetamidothiazole by 4-formamidothiazole.

EXAMPLE I

Anti-ulcer tablets are prepared by replacing 4-acetamidothiazole by 4-formamidothiazole in Example C.

EXAMPLE J

| Suspension | % w/v |
|---|---|
| Aluminium hydroxide gel B.P.5% $Al_2O_3$ | 80% = 4% $Al_2O_3$ |
| Magnesia Magma 12% w/v MgO | 10% |
| 4-diacetamidothiazole | 2.0% |
| Glycerin B.P. | 3.0% |
| Alcohol 60 O.P.* | 0.08% |
| Peppermint oil B.P. | 0.015% |
| Saccharin sodium B.P. | 0.01% |
| Methyl p-hydroxybenzoate sodium salt | 0.1% |
| Propyl p-hydroxybenzoate sodium salt | 0.02% |
| Butyl p-hydroxybenzoate sodium salt | 0.01% |
| Water q.s ad | 100.00% |

*O.P. denotes overproof. 60 O.P. represents 91% w/v Ethanol/Water.

The above suspension is prepared by the following procedure. Add to the Alumina gel Magnesia Magma followed by the thiazole dispersed in glycerin, the peppermint oil dissolved in alcohol, the saccharine sodium dissolved in water, and the p-hydroxybenzoate dissolved in water. Make up to volume of water and stir well. Dose: 5 ml. t.d.s.

EXAMPLE K

| Antacid Tablet (chewable) | |
|---|---|
| Saccharin | 1.0 mg. |
| Hydrated alumina sucrose powder | 750.0 mg. |
| 4-diacetamidothiazole | 100.0 mg. |
| Mannitol B.P. | 170.0 mg. |
| Maize starch B.P. dried | 30.0 mg. |
| Talc. purified B.P. | 28.0 mg. |
| Magnesium stearate B.P. | 20.0 mg. |
| Peppermint oil B.P. | 1.0 mg. |
| | 1100.0 mg. |

Antacid tablets of the above formulation are prepared by the following procedure.

Triturate peppermint oil with talc (screen 40 mesh). Add the triturate, the other ingredients to a blender and mix thoroughly.

Slug the powder to large hard slugs.

Granulate the slugs through a 14 mesh screen.

Compress the granules on a suitable compression machine to give tablets of the required size.

EXAMPLE L

| Anti-ulcer tablet (without antacid) | |
| --- | --- |
| | mg/tablet |
| 4-diacetamidothiazole | 100 mg. |
| Cellutab | 147.5 mg. |
| Mag. Stearate | 2.5 mg. |
| | 250.0 mg. |

The tablets are prepared by the following method.

Blend the ingredients in a suitable blender. Compress the blended ingredients on a suitable compression machine to form tablets of the above composition.

Cellutab is a commercial product comprising 90–2% dextrose. 3–5% maltose remainder higher glucose saccharides. Spray crystallised.

Preparation of the active ingredients

EXAMPLE 1

4-Acetamidothiazole (A) 4-Amino-2-bromothiazole hydrobromide (52 g, 0.2 m) was suspended in acetic anhydride (200 ml.) then treated dropwise with pyridine (100 ml.), maintaining the temperature at 0° C. by means of an ice bath. After the addition was complete, the reaction mixture was stirred for 2 hours at room temperature then poured onto 20% aqueous sodium acetate (2 l.) The solution was cooled, filtered and the precipitate washed with water (2 × 200 ml.). The product was air dried and recrystallised from acetone to give 4-acetamido-2-bromo-thiazole (35 g, 80%). m.p. 165° C.

Found: C, 27.5; H, 2.5; N, 12.7. $C_5H_5BrN_2OS$ requires C, 27.2; H, 2.3; N, 12.7%.

(B) A solution of 4-acetamido-2-bromo-thiazole (22 g., 0.2 m) and sodium acetate (8.2 g, 0.1 m) in methanol (600 ml) was hydrogenated at room temperature and 1 atm. pressure oven 10% palladium on carbon (5 g) until the theoretical uptake of hydrogen had occurred (about 3 hours). The catalyst was removed by filtration and the filtrate evaporated to dryness under reduced pressure. The residue was extracted with carbon tetrachloride (200 ml) in a Soxlet apparatus. The extract was cooled and the crystals removed by filtration to yield 4-acetamidothiazole (12 g, 78%). m.p. 176° C. Found: C, 41.8; H, 4.3; N, 19.3. $C_5H_6N_2OS$ requires: C, 42.2; H, 4.3; N, 19.7%.

EXAMPLE 2

4-Acetamido-5-methylthiazole (A) A suspension of 4-amino-2-bromo-5-methylthiazole hydrobromide (50 mM, 13.7 g) in acetic anhydride (100 ml) was treated dropwise with pyridine (10 ml) while cooling in an ice bath. After stirring for 1 hour the reaction mixture was poured onto 20% aqueous sodium acetate (1 l) and the aqueous solution extracted with dichloromethane (3 × 500 ml.). The combined organic layers were dried and evaporated under reduced pressure to give an oil which crystallised on trituration with ether. The crude product was recrystallised from ethanol to give the 4-acetamido-2-bromo-5-methylthiazole (11.7 g, 50%). mp 129°. (Found: C, 31.15; H, 3.15; N, 12.3. $C_6H_7BrN_2OS$ requires: C, 30.6; H, 3.0; N, 11.9%).

(B) A solution of 4-acetamido-2-bromo-5-methylthiazole (2.3 g) and sodium acetate (0.8 g) in methanol (60 ml) was hydrogenated at atmospheric pressure over 10% Pd/C catalyst until the theoretical uptake of hydrogen had occurred. The catalyst was removed by filtration and washed with methanol and the filtrate was evaporated to dryness. The residue was extracted with hot $CCl_4$ and the extracts were evaporated. The residue was recrystallised once from petroleum ether (b.p. 60°–80° C.) and once from hexane to give 4-acetamido-5-methylthiazole (0.2 g) m.p. 62°–4° C. (Found: C, 46.6; H, 5.3; N, 18.1. $C_6H_8N_2OS$ requires C, 46.1; H, 5.2; N, 17.9%).

EXAMPLE 3

(A) 2-Bromo-4-formamidothiazole

Acetic anhydride (100 ml) was cooled to 0° C. and treated with 98% formic acid (50 ml.). The resulting mixture was heated at 50° C. for 15 minutes then cooled to 0° C. To this solution of formic-acetic anhydride was added 4-amino-2-bromothiazole hydrobromide (26 g, 0.1 m) followed dropwise by pyridine (25 ml.). The reaction mixture was allowed to stand for 1 hour at room temperature then poured onto 20% aqueous sodium acetate solution (500 ml). The resulting crystals were removed by filtration, washed once with water (100 ml) then recrystallised from ethanol to give the 2-bromo-4-formamidothiazole (12 g, 58%). m.p. 167° C. d. (Found: C, 23.55; H, 1.6; N, 13.45. $C_4H_3N_2BrOS$ requires C, 23.2; H, 1.45; N, 13.5%).

(B) 4-Formamidothiazole

A suspension of 2-bromo-4-formamidothiazole (3 g) and sodium acetate in methanol (90 ml) was hydrogenated at atmospheric pressure over 10% Pd/C catalyst until the theoretical uptake of hydrogen had occurred. The catalyst was removed by filtration and washed with methanol and the filtrate was evaporated to dryness. The residue was continuously extracted in a Soxhlet apparatus with $CCl_4$ and the extracts were evaporated. The residue was recrystallised twice from $CCl_4$ to give 4-formamidothiazole (0.9 g) m.p. 99°–101° C. (Found: C, 37.4; H, 3.2; N, 22.0. $C_4H_4N_2OS$ requires C, 37.5; H, 3.1; N, 21.9%).

EXAMPLE 4

4-Acetamido-5-phenyl-thiazole

A solution of 4-acetamido-2-bromo-5-phenylthiazole (US Pat. No. 3,244,723) (5.5 g) and sodium acetate (1.55 g) in methanol (110 ml) was hydrogenated at atmospheric pressure over 10% Pd/C catalyst until the theoretical uptake of hydrogen had occurred. The catalyst was removed by filtration and washed with methanol and the filtrate was evaporated to dryness. The residue was recrystallised three times from benzene-petroleum ether (b.p. 60°–80° C.) to give 4-acetamido-5-phenylthiazole (1.5 g) m.p. 105°–7° C. (Found: C, 60.3; H, 4.65; N, 12.7. $C_{11}H_{10}N_2$ OS requires: C, 60.5; H, 4.6; N, 12.8%).

EXAMPLE 5

4-Propionamidothiazole

A solution of 2-bromo-4-propionamidothiazole (4g) and sodium acetate (1.4g) in methanol (100 ml.) was hydrogenated at atmospheric pressure over 10% Pd/C catalyst (1.0g) until the theoretical uptake of hydrogen had occurred. The catalyst was removed by filtration and washed with methanol and the extracts evaporated in vacuo. The residue was recrystallised twice from carbon tetrachloride to give the title compound (1.9g) m.p. 129°-32° C. (Found: C, 46.3; H, 5.2; N, 17.7. $C_6H_8N_2OS$ requires C, 46.1; H, 5.2; N, 17.9%).

EXAMPLE 6

(A) 2-Bromo-4-(cyclopropylcarboxamido)thiazole

4-Amino-2-bromothiazole hydrobromide (15.6 g.) and cyclopropylcarbonyl chloride (8.2 g.) were suspended in methylene chloride (100 ml.) with stirring and treated with pyridine (16 ml.) maintaining reaction temperature at 0° C. with an ice bath. After completing the addition, the reaction mixture was stirred at room temperature for 3 hours, then poured onto 20% aqueous sodium acetate and stirred for 30 minutes. The mixture was separated and the organic layer washed with 2N hydrochloric acid, water, sodium carbonate solution and water. The organic layer was dried and the solvent removed in vacuo and the residue recrystallised three times from carbon tetrachloride to give the title compound (7.3g) m.p. 152°-3° C. (Found: C, 34.7; H, 3.0; N, 11.4. $C_7H_7BrN_2OS$ requires C, 34.0; H, 2.9; N, 11.3%).

(B) 4-(Cyclopropylcarboxamido)thiazole

A solution of 2-bromo-4-(cyclopropylcarboxamido)-thiazole (4g) and sodium acetate (1.5g) in methanol (100 ml.) was hydrogenated at atmospheric pressure over 10% Pd/C catalyst (1g) until theoretical uptake of hydrogen had occurred. The catalyst was removed by filtration and washed with methanol and the filtrate evaporated to dryness in vacuo. The residue was recrystallised from carbon tetrachloride to give 4-(cyclopropylcarboxamido)thiazole (1.6g) m.p. 145°-7° C. (Found: C, 50.3; H, 4.9 N, 16.3. $C_7H_8N_2OS$ requires C, 50.0; H, 4.8; N, 16.6%).

EXAMPLE 7

4-Diacetylaminothiazole

A solution of 4-acetylaminothiazole (2.85g, 20mM) in a mixture of acetic anhydride (30ml) and pyridine (10 ml) was heated at 100° C. for 16 hours. The reaction mixture was cooled and poured onto an ice cold mixture of 20% aqueous sodium acetate (200ml) and chloroform (200 ml.). The layers were separated the organic layer was washed with water, dried (MgSO4) and the solvents removed under vacuum to give an oil. Trituration with hexane followed by recrystallisation from di-isopropyl ether gave the title compound (1.8g, 49%) m.p. 55° C. (Found: C, 45.8; H, 4.4; N, 15.5%. $C_7H_8N_2O_2S$ requires: C, 45.6; H, 4.4; N, 15.2%)

EXAMPLE 8

4-Butyramidothiazole

A solution of 2-bromo-4-butyramidothiazole (4g) and sodium acetate (1.35g) in methanol (100ml) was hydrogenated at atmospheric pressure over 10% Pd/C (1g) as catalyst until theoretical uptake of hydrogen had occurred. The catalyst was removed by filtration and washed with methanol and the extracts evaporated in vacuo. The residue was recrystallised from hexane and the crystals sublimed at 50° C. at 0.2mm and the sublimate recrystallised from carbon tetrachloride to give the title compound (1.1g) m.p. 63°-6° C. (Found: C, 49.0; H, 5.9; N, 16.5. $C_7H_{10}N_2OS$ requires C, 49.4; H, 5.9; N, 16.5%).

EXAMPLE 9

4-Chloroacetamidothiazole

A solution of 2-bromo-4-chloroacetamidothiazole (4g) and sodium acetate (1.15g) in methanol (100 ml) was hydrogenated at atmospheric pressure over 10% Pd/C catalyst (1 g) until theoretical uptake of hydrogen had occurred. The catalyst was removed by filtration and washed with methanol and the extracts evaporated to dryness in vacuo. The residue was recrystallised twice from carbon tetrachloride to give the title compound (1.6 g) m.p. 115°-119° C. (Found: C, 33.7; H, 2.9; N, 15.5. $C_5H_5ClN_2OS$ requires C, 34.0; H, 2.9; N, 15.8%).

The starting material was prepared as follows. 4-Amino-2-bromothiazole (15.6 g) and chloroacetyl chloride (7.6 g) were suspended in methylene chloride (100 ml) with stirring and treated with pyridine (16 ml) over 15 min., maintaining reaction temperature at 0° C. with an ice bath. After the addition was complete, the reaction mixture was stirred at room temperature for 3 hours, then poured onto 20% aqueous sodium acetate (500 ml) and stirred for 30 minutes. The mixture was separated and the organic layer washed with 2N hydrochloric acid, water, sodium carbonate solution and water. The organic layer was dried (MgSO4) and the solvent removed in vacuo and the residue recrystallised twice from carbon tetrachloride to give 2-bromo-4-chloroacetamidothiazole (5.1 g). m.p. 146°-8° C. (Found: C, 24.1; H, 1.7; N, 11.2. $C_5H_4ClBrN_2OS$ requires C, 23.5; H, 1.6; N, 11.0%).

I claim:

1. A pharmaceutical composition in oral dosage form for use in the treatment of ulcers or hypersecretion comprising a therapeutically effective amount of a compound of formula I

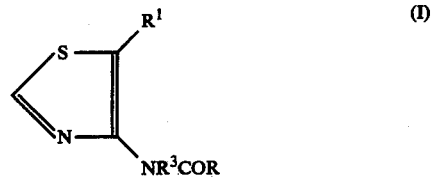

where $R^1$ is hydrogen, alkyl of 1-6 carbon atoms, or phenyl, R is hydrogen, n-alkyl of 1-4 carbon atoms, which may be substituted by chlorine, or cyclopropyl, $R^3$ is hydrogen or $COR^4$ where $R^4$ is as defined for R and R and $R^4$ may be the same or different and a pharmaceutically acceptable carrier.

2. A pharmaceutical composition as claimed in claim 1, in unit dosage form.

3. A pharmaceutical composition as claimed in claim 2 in the form of a tablet or capsule.

4. A pharmaceutical composition as claimed in claim 2, wherein the amount of compound I is from 50 to 250 mg per unit dose.

5. A pharmaceutical composition for use in the treatment of ulcers or hypersecretion comprising an antacid ingredient and a therapeutically effective amount of a compound of formula I

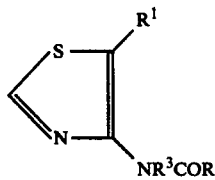

where $R^1$ is hydrogen, alkyl of 1–6 carbon atoms, or phenyl, R is hydrogen, n-alkyl of 1–4 carbon atoms, which may be substituted by chlorine, or cyclopropyl, $R^3$ is hydrogen or $COR^4$ where $R^4$ is as defined for R and R and $R^4$ may be the same or different.

6. A pharmaceutical composition as claimed in claim 1, wherein $R^1$ is hydrogen or methyl.

7. A pharmaceutical composition as claimed in claim 1, wherein R is hydrogen or methyl.

8. A pharmaceutical composition as claimed in claim 1 wherein $R^3$ is hydrogen.

9. A pharmaceutical composition as claimed in claim 8, wherein the compound of formula I is 4-acetamidothiazole.

10. A pharmaceutical composition as claimed in claim 8, wherein the compound of formula I is 4-acetamido-5-methylthiazole.

11. A pharmaceutical composition as claimed in claim 8, wherein the compound of formula I is 4-formamidothiazole.

12. A pharmaceutical composition as claimed in claim 8, wherein the compound of formula I is 4-propionamidothiazole.

13. A pharmaceutical composition as claimed in claim 1, wherein $R^3$ is $COR^4$ and $R^4$ is methyl.

14. A pharmaceutical composition as claimed in claim 13, wherein the compound of formula I is 4-diacetamidothiazole.

15. A method of treating ulcers or hypersecretion in an afflicted mammal which method comprises orally administering to said mammal an effective amount of a compound of formula I

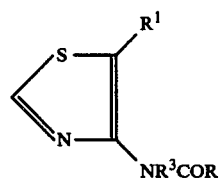

where $R^1$ is hydrogen, alkyl of 1–6 carbon atoms, or phenyl, R is hydrogen, n-alkyl of 1–4 carbon atoms, which may be substituted by chlorine, or cyclopropyl, $R^3$ is hydrogen or $COR^4$ where $R^4$ is as defined for R and R and $R^4$ may be the same or different.

16. A method as claimed in claim 15 wherein the compound of formula I is administered in a dose range of from 3 to 100 mg/kg.

17. A method as claimed in claim 16, wherein the compound is 4-acetamidothiazole, 4-formamidothiazole, 4-acetamido-5-methylthiazole or 4-diacetamidothiazole.

* * * * *